United States Patent [19]
Matsubara et al.

[11] Patent Number: 5,734,094
[45] Date of Patent: Mar. 31, 1998

[54] ION CURRENT DETECTOR DEVICE FOR USE IN AN INTERNAL COMBUSTION ENGINE

[75] Inventors: Yoshihiro Matsubara; Mamoru Kodera; Masahiro Ishikawa; Terumasa Tomita, all of Nagoya, Japan

[73] Assignee: NGK Spark Plug Co., Ltd., Nagoya, Japan

[21] Appl. No.: 797,938

[22] Filed: Feb. 12, 1997

Related U.S. Application Data

[60] Continuation-in-part of Ser. No. 462,284, Jun. 5, 1995, which is a division of Ser. No. 250,670, May 27, 1994.

[30] Foreign Application Priority Data

May 31, 1993 [JP] Japan ................. 5-129534
May 31, 1993 [JP] Japan ................. 5-129796

[51] Int. Cl.⁶ ................................... F02P 17/12
[52] U.S. Cl. ........................... 73/35.08; 324/402
[58] Field of Search ................... 73/35.06, 35.07, 73/35.08, 116, 117.3; 324/393, 398, 399, 402

[56] References Cited

U.S. PATENT DOCUMENTS

| | | | |
|---|---|---|---|
| 3,286,164 | 11/1966 | De Huff | 324/398 |
| 4,232,545 | 11/1980 | Dobler et al. | 73/35 |
| 4,307,603 | 12/1981 | Dobler et al. | 73/35 |
| 4,312,215 | 1/1982 | Dobler et al. | 73/35 |
| 5,180,983 | 1/1993 | Murata et al. | 324/399 |
| 5,180,984 | 1/1993 | Murata et al. | 324/399 |
| 5,237,280 | 8/1993 | Arnold et al. | 324/393 |
| 5,377,653 | 1/1995 | Hamada et al. | 73/116 |
| 5,383,350 | 1/1995 | Bennett et al. | 324/402 |

FOREIGN PATENT DOCUMENTS

| | | |
|---|---|---|
| 51-104142 | 9/1976 | Japan. |
| 59-36391 | 9/1984 | Japan. |

*Primary Examiner*—Elizabeth L. Dougherty
*Assistant Examiner*—Eric S. McCall
*Attorney, Agent, or Firm*—Sughrue, Mion, Zinn, Macpeak & Seas, PLLC

[57] ABSTRACT

An ion current detector device for an internal combustion engine, including: a spark plug having a metallic shell in which a tubular insulator is disposed, a center electrode extending in an axial direction of the tubular insulator and having a front end, a ground electrode which forms a spark gap (G1) with the front end of the center electrode, and at least one slanted bore provided in the metallic shell which is slanted inwardly against the axial direction with respect to the center electrode. An ion current detector electrode is provided within the slanted bore of the metallic shell and located proximate to the front end of the center electrode of the spark plug so as to form an ion current gap (G2) therebetween, the ion current gap (G2) being dimensionally wider than the spark gap (G1), and the spark plug being connected to an ignition circuit to be provided in a cylinder of the internal combustion engine. An operational rod is provided for initially moving the ion current detector in the axial direction within the slanted bore thereby to microadjust a width of the ion current gap (G2) and then firmly positioning the ion current detector electrode within the slanted bore. An ion current detector circuit is provided between the ion current detector electrode and the ground for detecting an ion current flowing between the center electrode and the ground through the ion current gap (G2) depending on a voltage difference therebetween.

6 Claims, 7 Drawing Sheets

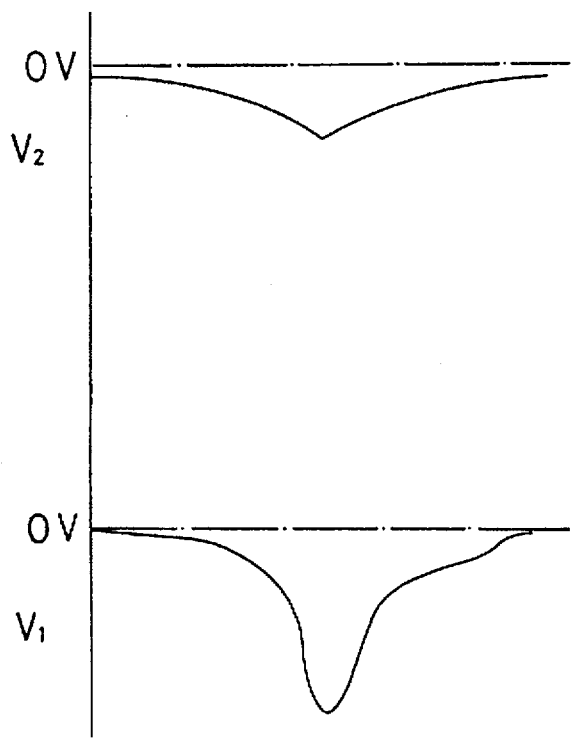

ION CURRENT DETECTOR DEVICE FOR USE IN AN INTERNAL COMBUSTION ENGINE

This is a Continuation-in-Part of application Ser. No. 08/462,284 filed Jun. 5, 1995, which is a divisional of application Ser. No. 08/250,670, filed May 27, 1994.

BACKGROUND OF THE INVENTION

1. Field of the Invention

This invention relates to an ion current detector device which measures an ion current in an inside of a cylinder or an exhaust passage of an internal combustion engine so as to detect its burning conditions such as a misfire.

2. Description of Prior Art

In an ion current detector device for an internal combustion engine, an ion current detector electrode and an ion current electrode have been arranged to be exposed to an inside of a cylinder or an exhaust passage of an internal combustion engine. Several hundred volts are applied across the two electrodes to detect an intensity of electrical current caused from ionized particles in burning gas of an air-fuel mixture or exhaust gas.

In this type of ion the ion current detector device, an intensity of ion current is detected between the engine body and a common electrode used in common with respect to an ion current power source circuit and an ion current detector circuit. This makes the ion current detector circuit more complicated so as to have a low reliability and a high cost when putting the device into practical use in an internal combustion engine.

Therefore, it is one of objects of the invention to provide an ion current detector device which is capable of structurally simplifying an ion current detector circuit, and manufacturing it at low cost with high reliability.

SUMMARY OF THE INVENTION

According to the invention, there is provided an ion current detector device for an internal combustion engine including an ion voltage electrode provided so that its front end is exposed to an inside of a cylinder or an exhaust passage of an internal combustion engine. An ion current power source is connected to the ion voltage electrode. An ion current detector electrode is provided to form an ion current gap with the front end of the ion voltage electrode. A voltage detector circuit is provided between the ion current detector electrode and a resistor which is connected across the ion current detector electrode and the ground.

With the use of the ion current detector circuit having the resistor and the voltage detector circuit each connected between the ion current detector electrode and the ground, it is possible to structurally simplify the ion current detector circuit, and reduce the cost with easy maintenance.

With a plurality of ion current detector electrodes circumferentially arranged with the ion voltage electrode as a central portion, it is possible to detect the intensity of ion current with high accuracy, and detecting the direction in which combustion flames spread in the cylinder of the internal combustion engine.

According to the present invention, there is provided an ion current detector device for an internal combustion engine, comprising a spark plug including a center electrode extending in an axial direction and having a front end, a ground electrode, and at least one slanted bore which is slanted inwardly against the axial direction with respect to the center electrode; an ion current detector electrode provided within the slanted bore of the spark plug and located proximate to the front end of the center electrode of the spark plug so as to form an ion current gap therebetween, the spark plug being connected to an ignition circuit and provided in a cylinder of the internal combustion engine; means for initially axially moving the ion current detector electrode within the slanted bore thereby to micro-adjust a width of the ion current gap and then firmly positioning the ion current detector electrode within the slanted bore; and an ion current detector means, provided between the ion current detector electrode and ground, for detecting an ion current flowing between the center electrode and ground through the ion current gap depending on a voltage difference therebetween.

In the presence of the ionized particles between the center electrode and the ion current detector electrode upon completing the normal combustion in the cylinder of the internal combustion engine, the ionized particles cause an electrical resistance of the ion current gap between the two electrodes to decrease. This makes it possible to induce an ion current jumping the gap to flow to the center electrode by way of the ion current detector circuit and the ion current detector electrode. As a result, an intensity of the ion current is measured by the ion current detector circuit without particularly providing an ion current power source, and thus enabling to detect a burning condition such as misfire in the cylinder of the internal combustion engine with a simplified circuit.

With the ion current detector circuit having a resistor connected between the ion current detector electrode and the ground, and a voltage detector circuit which detects an intensity of current flowing across the resistor and the ion current detector electrode, it is possible to simplify the ion current detector circuit, and produces it at low cost.

With the high voltage diode connected between the center electrode of the spark plug and the ignition circuit so as to prevent current flowing back to the ignition circuit, it is possible to avoid a reverse-polarity ion current from occurring in the ion current detector circuit so as to obtain a highly accurate detection, while at the same time, insuring a high voltage applied to the spark plug.

These and other objects and advantages of the invention will be apparent upon reference to the following specification, attendant claims and drawings.

BRIEF DESCRIPTION OF THE DRAWINGS

FIGS. 6a and 6b are graphs characteristic of an ion current;

FIG. 7b is a bottom plan view of the ion current detector device as viewed along the line 7A—7A of FIG. 7a.

DETAILED DESCRIPTION OF PREFERRED EMBODIMENT OF THE INVENTION

Figure 1:
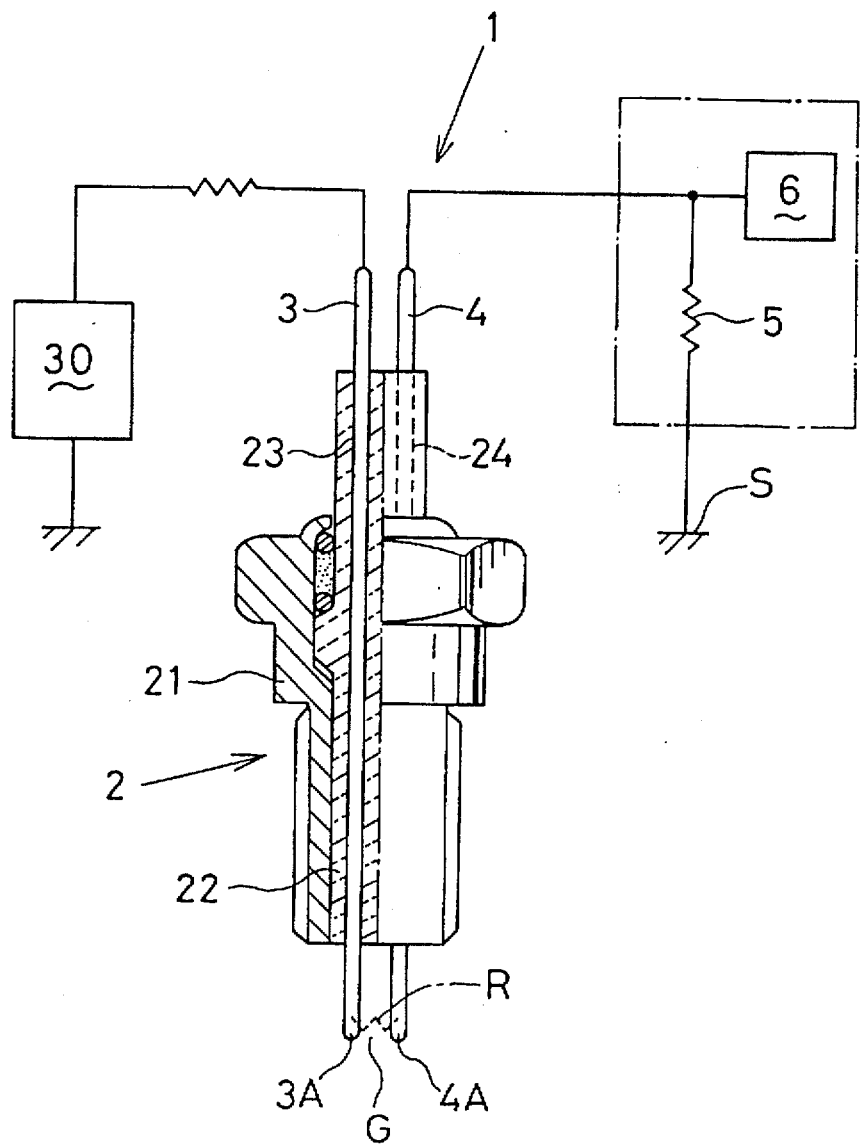
FIG. 1 is a schematic view of an ion current detector device according to a first embodiment of the invention.

Referring to FIG. 1 which shows an ion current detector device 1 used for an internal combustion engine, numeral 2 designates an ion plug which is incorporated into a cylinder head (not shown) of the internal combustion engine. The ion plug 2 has a metallic shell 21 in which an elongated insulator 22 is placed. In the insulator 22, axial bores 23, 24 are provided in parallel with each other. Within the axial bore 23, an ion voltage electrode 3 is tightly placed to be electrically connected to a D.C. or A.C. type current power source 30 (several tens to hundreds of volts), while an ion current detector electrode 4 is firmly placed within the axial bore 24 so as to form an ion current gap G between a front end 3A of the former electrode 3 and a front end 4A of the latter electrode 4. In this instance, both the front ends 3A, 4A of the electrodes 3, 4 are directly exposed to an inside of a cylinder of the internal combustion engine. The front ends 3A, 4A of the electrodes 3, 4 may be directly exposed to an exhaust passage through which an exhaust gas passes from the cylinder of the internal combustion engine.

Meanwhile, a resistor 5 is provided between the ion current detector electrode 4 end the ground S, and a voltage detector circuit 6 is provided between the resistor 5 and the ion current detector electrode 4.

Figure 2A:
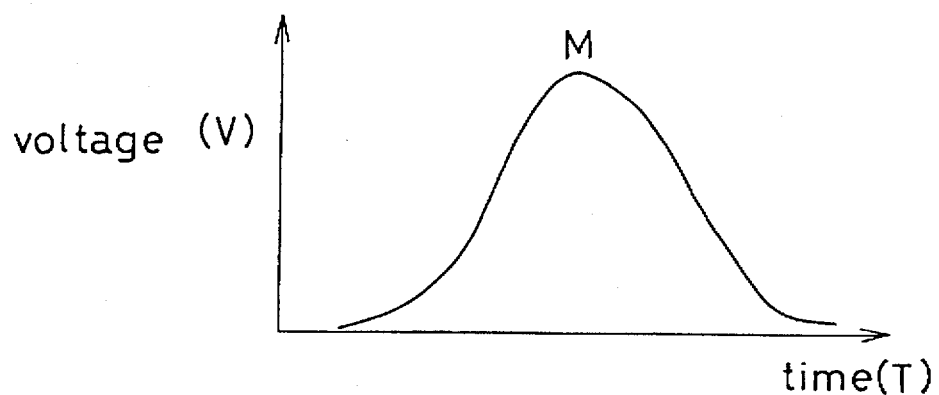
FIGS. 2a and 2b are graphical representations characteristic of an ion current.

Upon running the internal combustion engine, a spark plug ignites an air-fuel mixture vapor injected into the cylinder of the internal combustion engine in accordance with an ignition timing determined depending on the running condition of the internal combustion engine. When the air-fuel mixture vapor is normally ignited in the cylinder of the internal combustion engine, ionized particles in the combustion gas decreases an electrical resistance of the ion current gap G to break down its electrical insulation so as to permit an ion current flowing through the ion current gap G. In this moment, an electrically live path is formed from the current power source 30 to the ground S by way of the electrode 3, the ion current gap G, the electrode 4 and the resistor 5, thereby permitting a high level ion current to flow therethrough. As shown at M in FIG. 2a, the ion current is detected as a variation of voltage by voltage detector circuit 6 through a divider circuit provided by the resistor 5 and a resistor R of the ion current gap G.

Figure 2B:
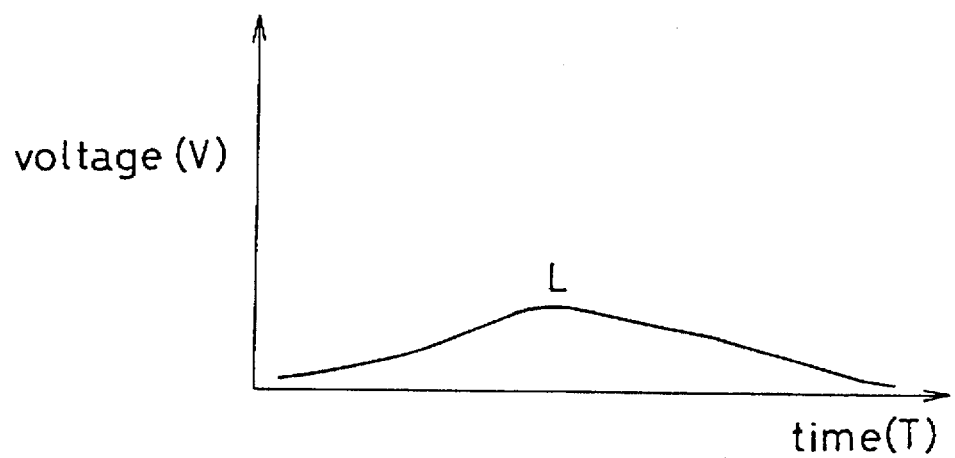

When the spark plug fails to ignite the air-fuel mixture vapor due to a malfunction of its ingnition circuit or an insufficient spark discharge of the spark plug, substantially no ion current is permitted to flow through the ion current gap G due to an absence or insufficient presence of the ionized particles in the air-fuel mixture vapor. As a result, the voltage detector circuit 6 detects a low level ion current flowing through the ion current gap G as shown at L in FIG. 2b.

That is to say, it is possible to detect a misfire in the cylinder of the internal combustion engine depending on whether or not the ion current level is more than a predetermined threshold. It is noted that it is possible to recognize a burning condition in the cylinder of the internal combustion engine by detecting a rising-up curve, a slowing-down curve, a sustaining time length, an integral curve value, or a time length duration required to reach a predetermined level characteristic of the graphical representation shown in FIGS. 2a, 2b.

Figure 3A:
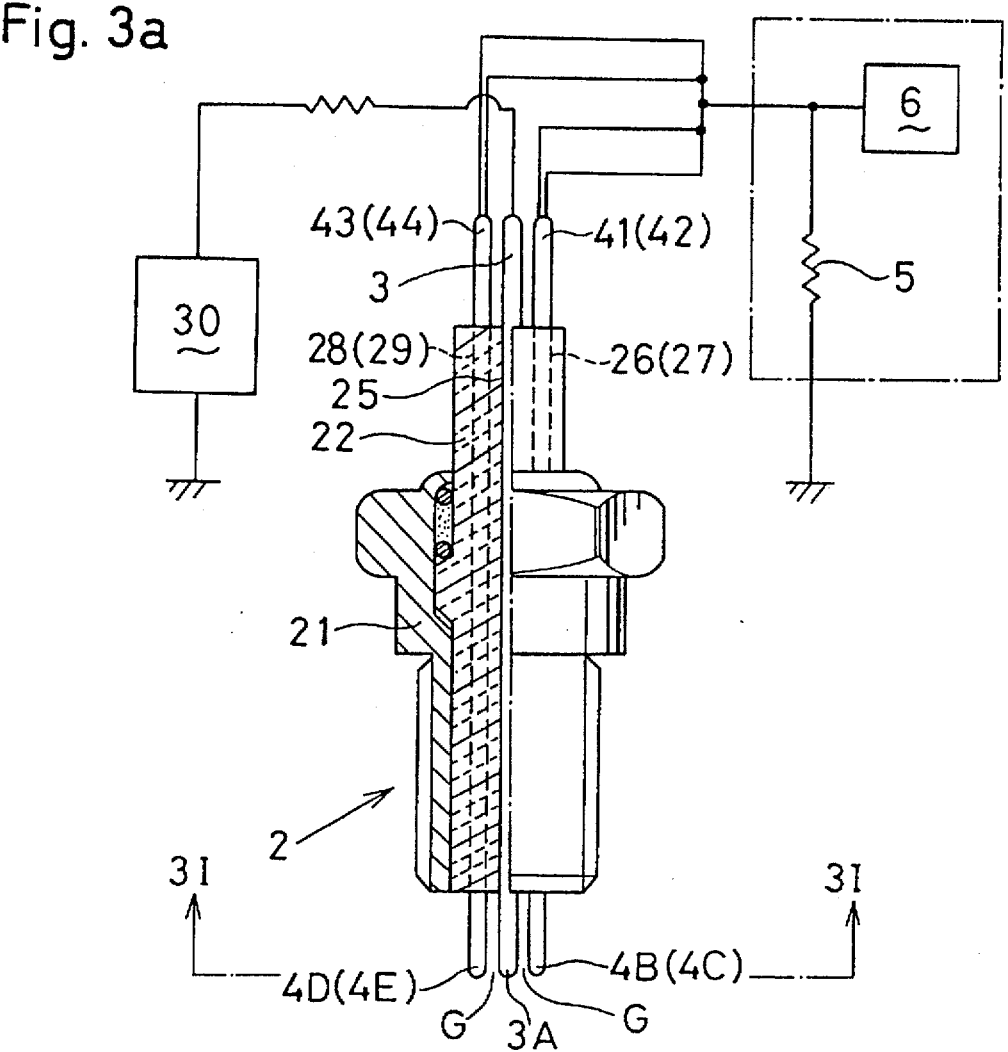
FIG. 3a is a schematic view of an ion current detector device according to a second embodiment of the invention.
Figure 3B:
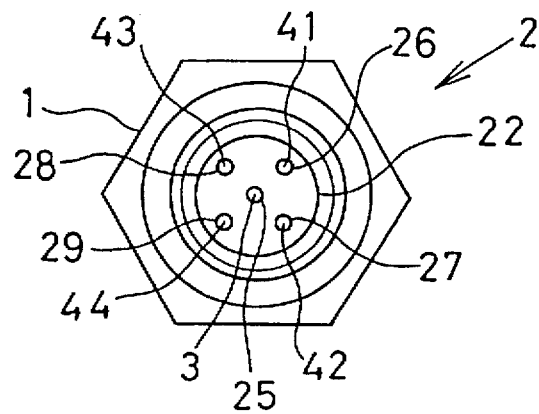
FIG. 3b is a bottom plan view of the ion current detector device as viewed along the line 3I—3I of FIG.

FIGS. 3a and 3b show a second embodiment of the invention in which an elongated insulator 22 has a central bore 25, and circumferentially having a plurality of axial bores 26~29 with the bore 25 as a center. The ion voltage electrode 3 is firmly placed in the central bore 25, while ion current detector electrodes 41~44 are solidly placed in the axial bores 26~29, respectively. The number of the ion current detector electrodes is chosen at discretion such as two, three, five or more. The ion current gap G is defined between the front end 3A of the electrode 3 and front ends 4B~4E of the electrodes 41~44. In this instance, the ion current detector electrodes 41~44 may be provided by an insulator in the metallic shell 21, otherwise they may be provided in another ion plug discrete from the ion plug 2 in which the ion voltage electrode 3 is placed.

In so doing, it is possible to detect the direction in which the combustion flames spread in the cylinder of the internal combustion engine by multiplying the number of the ion current detector electrodes 41~44. Further, the added number of the electrodes 41~44 makes it possible to increase the chances of detecting the ion current, thereby enhancing the ion current detection accuracy when the ionized particles are not ubiquitously present around the ion current detector electrodes 41~44 by the combustion condition.

Figure 4:
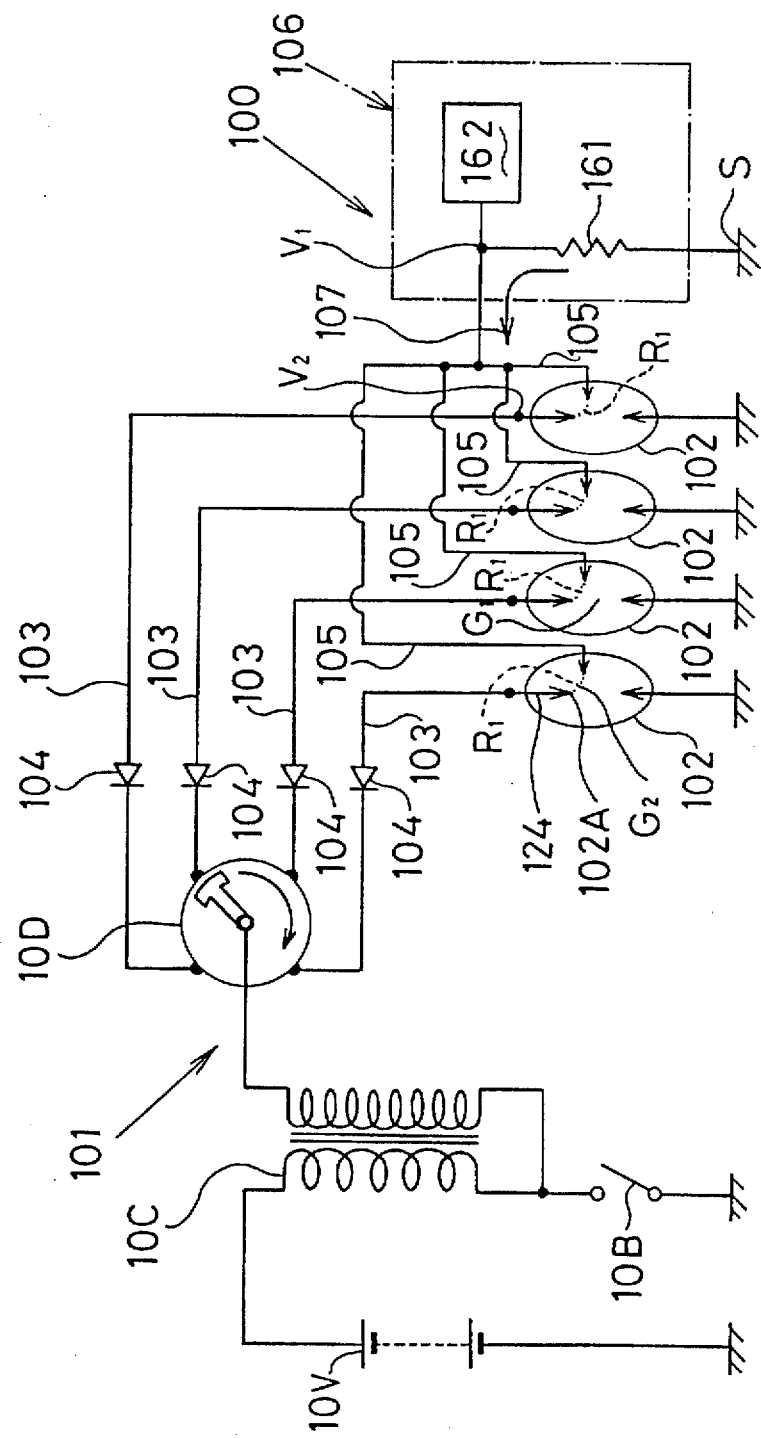
FIG. 4 is a schematic view of an ion current detector device incorporated into an internal combustion engine according to a third embodiment of the invention.

FIG. 4 shows a third embodiment of the invention in which an ion current detector device 100 is incorporated into an ignition circuit 101 for an internal combustion engine. Numeral 10C designates an ignition coil which steps up a primary voltage supplied from a vehicular battery cell 10V to establish a spark plug voltage. Numeral 10B designates a primary current on-off interrupter device used for the ignition coil 10C. Numeral. 10D is a distributor through which the spark plug voltage is applied to a spark plug 102 mounted on a cylinder head of the internal combustion engine. A spark plug voltage circuit 103 is provided to electrically connect the distributor 10D to the spark plug 102. A high voltage diode 104 is provided between the distributor 10D and the spark plug 102 so as to prevent a current flowing back toward the distributor 10D.

Figure 5:
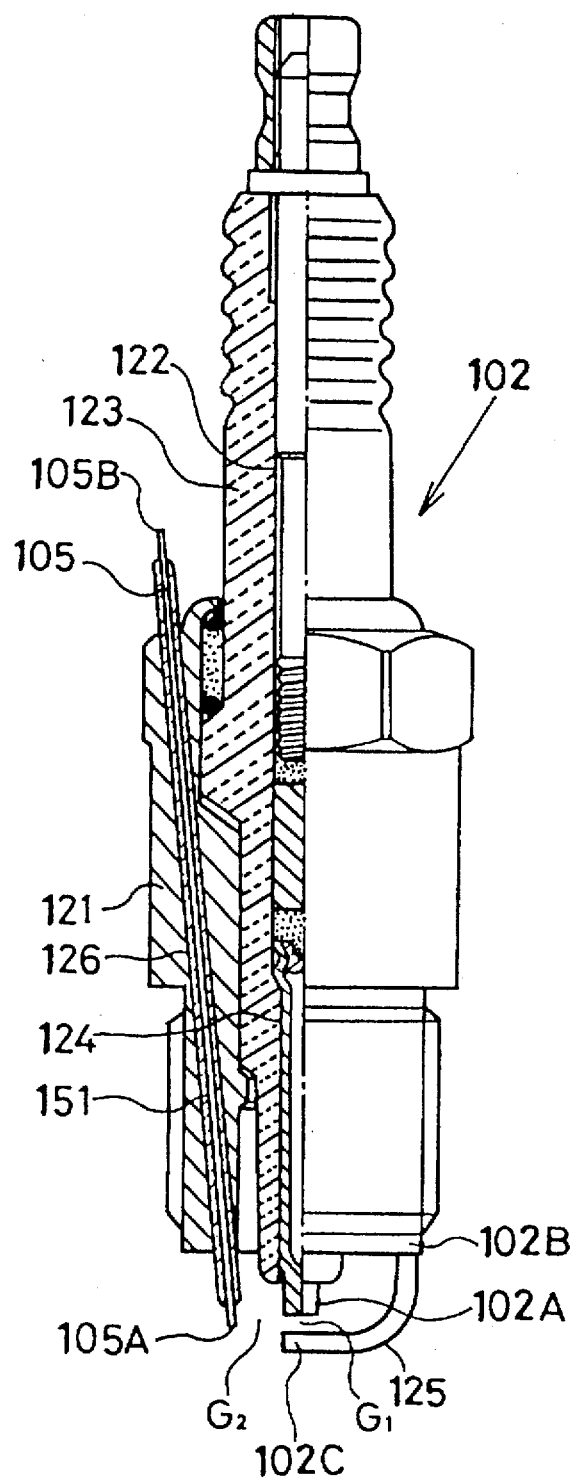
FIG. 5 is a plan view a spark plug according to the third embodiment of the invention, but its left half is sectioned.

Meanwhile, the spark plug 102 has a metallic shell 121 in which a tubular insulator 123 is fixedly placed as shown in FIG. 5. Within an axial bore 122 of the insulator 123, a center electrode 124 is placed whose front end 102A forms a spark gap G1 with a front end 102C of a L-shaped ground electrode 125 welded to a front end surface 102B of the metallic shell 121. A bore 126 is provided in the metallic shell 121 somewhat slantwisely against its axial direction. Within the bore 126, an ion current detector electrode 105 is ultimately tightly placed which is coated by an insulation film 151. Between a front end 105A of the electrode 105 and the front end 102A of the center electrode 124, an ion current gap G2 is formed which is greater in width than the spark gap G1. The ion current detector device 100 includes the ion current detector electrode 105 and an ion current detector circuit 106 connected between a rear end 105B of the ion current detector electrode 105 and the ground S. The ion current detector circuit 106 has a resistor 161 and a voltage detector circuit 162 which detects a voltage change between the resistor 161 and the rear end 105B of the ion current detector electrode Upon operating the ignition circuit 101 to keep running the internal combustion engine, the primary current on-off interrupter device 10B induces the spark plug voltage (10, 000 V or more) in the spark plug voltage circuit 103 which is equivalent to a secondary circuit of the ignition coil 10C. The spark plug voltage is supplied to a point V2 of the center electrode 124 of the spark plug 102 by way of the distributor 10D and the high voltage diode 104.

This causes to establish a spark discharge at the spark gap G1 so as to ignite an air-fuel mixture vapor injected into the cylinder of the internal combustion engine. Upon normally igniting the air-fuel mixture vapor, the presence of the ionized particles in the combustion gas makes it possible to drop an electrical resistance R1 of the ion current gap G2 to break down its insulation so as to permit an ion current flowing through the gap 92.

In this moment, an electrically live path is formed from the ground S to the center electrode 124 by way of the resistor 161, the electrode 105, the ion current gap G2, and thus permitting a high level ion current flowing in the direction of an arrow 107 shown in FIG. 4. As shown in FIG. 6b, the high level ion current is detected at a point V1 in terms of voltage by the voltage detector circuit 162 through a divider circuit provided by the resistor 161 and a resistor R1 of the ion current gap G2.

The spark plug voltage is in the side of relatively stable negative polarity caused from an early stage of an inductive discharge subsequent to capacitive discharge when the high voltage is applied to the center electrode in the side of negative polarity. However, the spark plug voltage is likely to fluctuate before the start and after an end of the spark discharge between the electrodes 124, 125, and thus oscillating the ion current to change its polarity. As a result, an accurate ion current detection is possible only during short period at the time of around the ignition. The provision of the high voltage diode 104 makes it possible to eliminate a reverse polarity voltage of the oscillating spark plug voltage so as to enable to an accurate ion current detection after the end of the spark discharge between the electrodes 124, 125.

When the spark plug fails to ignite the air-fuel mixture vapor due to malfunction of its ingnition circuit or an insufficient spark discharge of the spark plug, substantially no ion current is permitted to flow through the ion current gap G2 due to an absence or insufficient presence of the ionized particles in the air-fuel mixture vapor. As a result, the voltage detector circuit 162 detects a low level ion current flowing through the ion current gap G2 as shown in FIG.

That is to say, it is possible to detect a misfire in the cylinder of the internal combustion engine depending on whether or not the ion current level is more than a predetermined threshold. It is noted that it is possible to recognize the burning conditions in the cylinder of the internal combustion engine by detecting a rising-up curve, a sloping-down curve, a sustaining time length, an integral curve value, or a time length duration required to reach a predetermined level characteristic of the Graphical representation shown in FIGS. 6a, 6b.

Figure 7A:
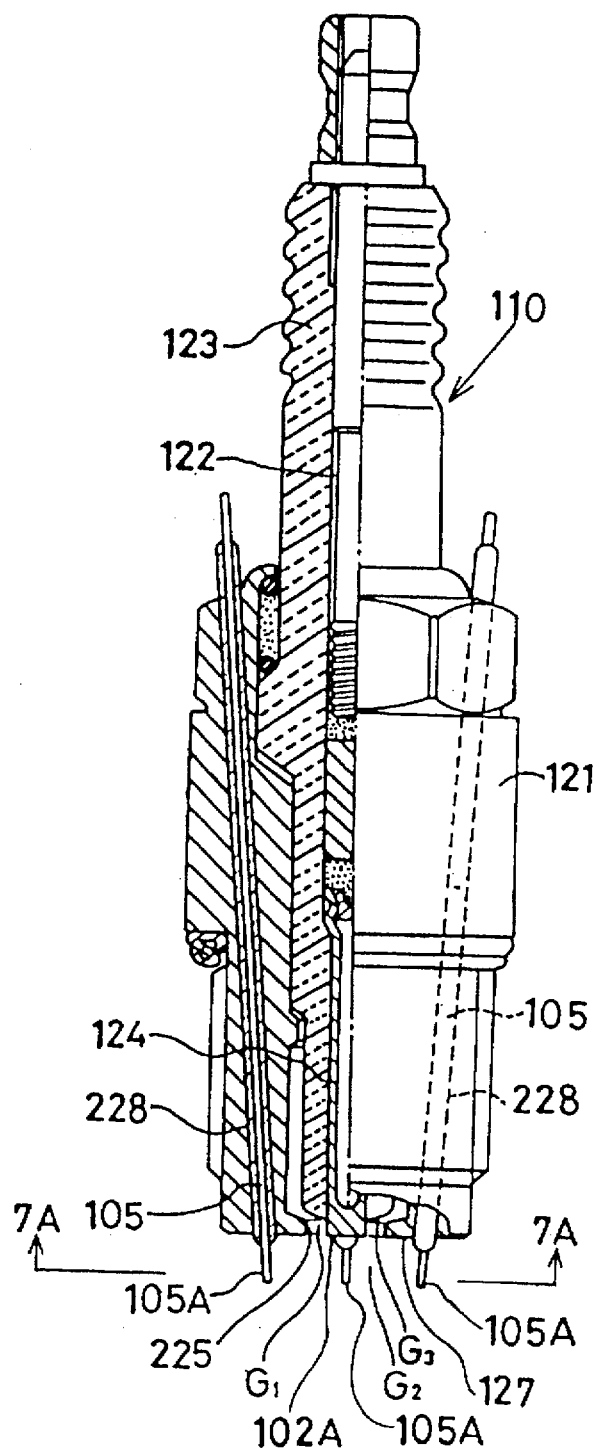
FIG. 7a is a longitudinal cross sectional view of an ion current detector device according to a fourth embodiment of the invention.
Figure 7B:
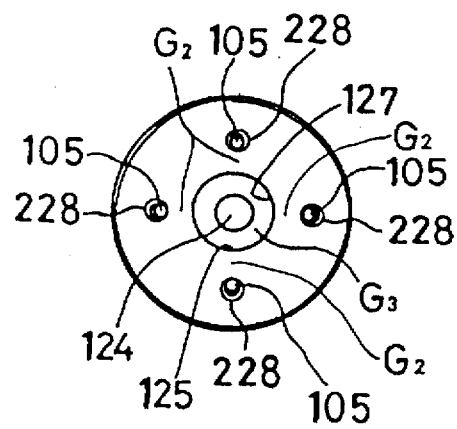

FIGS. 7a and 7b show a fourth embodiment of the invention in which a spark plug 110 has an annular ground electrode 225 provided at an front end 127 of the metallic shell 121 instead of the L-shaped ground electrode 125. This arrangement makes it possible to form a semi-creeping spark discharge gap G3 between an inner wall of the ground electrode 225 and the front end 102A of the center electrode 124. Four bores are provided in the metallic shell 121 slightly oblique against its axial direction as designated by numeral 228. In each of the four bores 228, the ion current detector electrode 105 is ultimately firmly placed to define the ion current gap G2 between the front end 102A of the center electrode 124 and the front end 105A of the ion current detector electrode 105. In this instance, the ion current detector electrode 105 may be provided in the insulator 123 instead of the metallic shell 121.

Thus the added number of the ion current detector electrodes makes it possible to increase the chances of detecting the ion current, and enhancing the ion current detection accuracy when the ionized particles are not ubiquitously present around the ion current detector electrode 105 by the combustion condition.

Further, in the embodiments shown in FIG. 5 and in FIGS. 7a, 7b, it is preferable to provide means for initially axially moving the ion current detector electrode 105 within the slanted bore(s) (126; 228) thereby to micro-adjust a width of the ion current gap $G_2$ and then firmly positioning or fixing the ion current detector electrode 105 within the slanted bore(s) (126; 228).

The means for initially axially moving the ion current detector electrode 105 includes the thin insulation film 151 (see FIG. 5) which is coated over an outer surface of the ion current detector electrode 105. The ion current detector electrode 105 is inserted axially into the slanted bore 126 (or plural electrodes 105 into respective bores 228) to form an ion current gap $G_2$ between its front end 105A and a front end 102A of the center electrode 102.

A thermosetting plastic or inorganic heat-resistant adhesive is applied between the insulation film 151 of the ion current detector electrode 105 and an inner wall of the slanted bore 126 (or bores 228). During the time of desiccating the adhesive at the assembling process, the electrode 105 can be axially moved to micro-adjust the ion current gap $G_2$ while the adhesive is still rich in fluidity.

Alternatively, an inner surface of the slanted bore 126 (or each of the bores 228) has a female thread while an outer surface of the ion current detector electrode 105 has a male thread. The electrode 105 is coated with the insulation film 151 and screwed into the slanted bore 126 (or each of the bores 228) while applying the adhesive between the insulation film 151 of the ion current detector electrode 105 and the inner wall of the slanted bore 126 (or bores 228). By turning the ion current detector electrode 105 about its axis before the adhesive is solidified during the assembling process, it is possible to axially move the ion current detector electrode 105 so as to micro-adjust the ion current gap $G_2$.

It is appreciated that a changing rate of the voltage may be detected by the ion current detector circuit 106 instead of merely measuring the peak voltage.

While the invention has been described with reference to the specific embodiments, it is understood that this description is not to be construed in a limiting sense in as such as various modifications and additions to the specific embodiments may be made by skilled artisan without departing from the spirit and scope of the invention.

What is claimed is:

1. An ion current detector device for an internal combustion engine, comprising:
   a spark plug including a metallic shell in which a tubular insulator is disposed, a center electrode extending in an axial direction of the tubular insulator and having a front end, a ground electrode which forms a spark gap (G1) with the front end of the center electrode, and at least one slanted bore provided in the metallic shell and which is slanted inwardly against the axial direction with respect to the center electrode;
   an ion current detector electrode provided within the slanted bore of the metallic shell and located proximate to the front end of the center electrode of the spark plug so as to form an ion current gap (G2) therebetween, the ion current gap (G2) being dimensionally wider than the spark gap (G1), and the spark plug being connected to an ignition circuit and provided in a cylinder of the internal combustion engine;

means for initially moving the ion current detector electrode in the axial direction within the slanted bore thereby to micro-adjust a width of the ion current gap (G2) and then firmly positioning the ion current detector electrode within the slanted bore; and an ion current detector means, provided between the ion current detector electrode and the ground, for detecting an ion current flowing between the center electrode and the ground through the ion current gap (G2) depending on a voltage difference therebetween.

2. An ion current detector device for an internal combustion engine as recited in claim 1, wherein the ion current detector means comprises a resistor connected between the ion current detector electrode and ground, and further having a voltage detector means which detects an intensity of the current flowing across the resistor and the ion current detector electrode.

3. An ion current detector device for an internal combustion engine as recited in claim 2, wherein a diode is connected between the center electrode of the spark plug and the ignition circuit so as to prevent a current from flowing back to the ignition circuit.

4. An ion current detector device for an internal combustion engine as recited in claim 1, wherein the ion current detector electrode comprises a plurality of current detector electrodes circumferentially arranged around the periphery of the center electrode.

5. An ion current detector device for an internal combustion engine as recited in claim 1, wherein the ground electrode is formed into an annular configuration, and is located between said center electrode and a plurality of current detector electrodes.

6. An ion current detector device for an internal combustion engine as recited in claim 1, wherein said ion current detector means comprises an ion current detector circuit.

* * * * *